United States Patent [19]
Brauer et al.

[11] Patent Number: 5,387,979
[45] Date of Patent: Feb. 7, 1995

[54] SPECTROPHOTOMETRIC METHOD AND SPECTROPHOTOMETER FOR PERFORMING THE METHOD

[75] Inventors: Stefan Brauer, Södra Sandby; Rolf Castor, Hägersten; Anders Linge, Kävlinge; Sven-Gunnar Olson, Arlöv, all of Sweden

[73] Assignee: Siemens-Elema AB, Solna, Sweden

[21] Appl. No.: 108,799

[22] Filed: Aug. 19, 1993

[30] Foreign Application Priority Data

Aug. 21, 1992 [SE] Sweden .................. 9202402

[51] Int. Cl.6 .............. G01N 21/31; G01N 21/35; G01J 3/427
[52] U.S. Cl. .............. 356/435; 250/339.13; 356/437
[58] Field of Search .............. 356/435, 437; 250/339.12, 339.13

[56] References Cited

U.S. PATENT DOCUMENTS 3,877,812  4/1975  Thompson .............. 356/51 X
4,427,889  1/1984  Müller .............. 128/633 X

FOREIGN PATENT DOCUMENTS 0196993  3/1986  European Pat. Off. .
0385256  2/1990  European Pat. Off. .
2102942  2/1983  United Kingdom .
WO82/03687  10/1982  WIPO .

*Primary Examiner*—Vincent P. McGraw
*Attorney, Agent, or Firm*—Hill, Steadman & Simpson

[57] ABSTRACT

In a spectrophotometer for measuring the concentration of a specific substance, a pulsating (modulated) source of radiation gives rise to an alternating current component, a direct current component and a dark signal component in a measurement signal. The response time for changes in the concentration of the specific substance is reduced while the measurement signal's signal-to-noise ratio is simultaneously improved when the pulsation frequency is from 50 to 1000 Hz, and the direct current component in the measurement signal is filtered out for normalization by a reference signal in a signal analyzer so the concentration of the specific substance can be calculated.

16 Claims, 3 Drawing Sheets

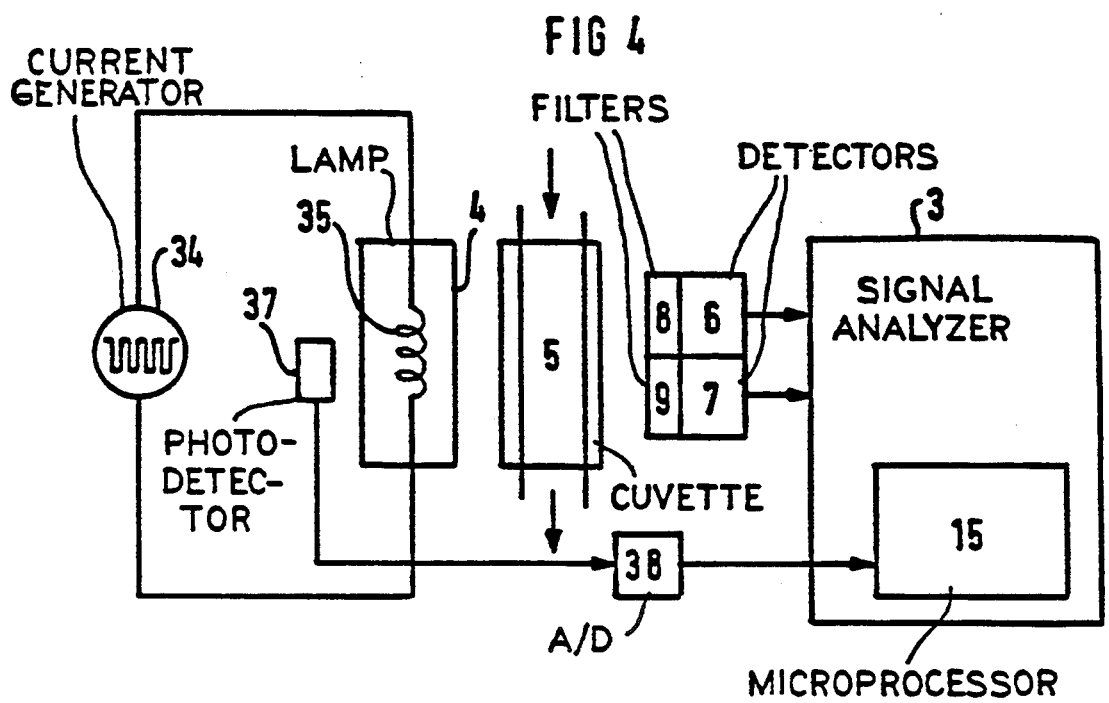

SPECTROPHOTOMETRIC METHOD AND SPECTROPHOTOMETER FOR PERFORMING THE METHOD

BACKGROUND OF THE INVENTION

1. Field of the Invention

The present invention relates to spectrophotometric methods and spectrophotometers.

2. Description of the Prior Art

For determining the concentration of a specific substance, it is known to generate radiation, whose intensity is modulated to a defined degree of modulation, which passes through the specific substance. A measurement signal for a radiation wavelength at which the specific substances absorbs the radiation is generated by a first detector, and a reference signal for a radiation wavelength, other than the specific substance's radiation wavelength, is generated by a second detector and the concentration of the specific substance is determined with a signal analyzer from the measurement signal and the reference signal.

European Application 0 196 993 describes a known spectrophotometer operating in this manner. The known spectrophotometer is a gas concentration measuring apparatus which measures the concentration of a specific, non-elementary polyatomic gas in a gas mixture. The gas passes through a cuvette which is irradiated by a pulsating source of radiation. The radiation then passes a first interference filter which is transparent to a wavelength at which the specific gas absorbs radiation and strikes a first detector which then generates a measurement signal. Next to the first interference filter is arranged a second interference filter which is transparent to a wavelength at which the specific gas does not absorb radiation. The radiation which passes the second interference filter strikes a second detector which then generates a reference signal. The measurement signal and the reference signal are amplified and filtered in respective capacitors, the alternating current part of the measurement signal and the reference signal being filtered out. Each signal is synchronously rectified, whereupon the ratio between the two signals is formed. The ratio signal then constitutes a normalized measurement signal which is independent of detector temperature (provided the detectors change temperature uniformly), the aging of the radiation source, etc. The normalized measurement signal only depends on the concentration which can thereby be calculated.

The source of radiation in the known spectrophotometer pulsates at a frequency of primarily 1–30 Hz. Since the source of radiation is pulsed, measurement results are not affected by interference, such as radiation leakage from other sources acting on the detectors etc. The radiation consists of an alternating intensity component superimposed on a fixed intensity component, so that the detectors thereby generate an alternating current component and a direct current component. The direct current component is eliminated in the capacitor, but since both components in the measurement signal depend to the same extent on the concentration of the specific substance, rapid fluctuations in concentration can result in the direct current component passing the capacitor, thereby producing an erroneous value for the concentration. In addition, the response time for changes in concentration is dependent on the frequency used. The most rapid response in the known spectrophotometer is attained at 30 Hz. An increase in the frequency of the known spectrophotometer would reduce the modulation of, and hence variations in, the source of radiation, thereby reducing the alternating current component. As a result, errors caused by the passage of the direct current component through the capacitor when there are rapid fluctuations in concentration would, in turn, be larger, and the signal-to-noise ratio of the direct current component would be impaired, since the direct current component would decline at higher frequencies.

SUMMARY OF THE INVENTION

An object of the present invention is to provide a spectrophotometric method which is capable of determining the concentration of the specific substance with a high degree of accuracy, a large signal-to-noise ratio and a fast response time.

It is also an object of the present invention to provide a spectrophotometer for performing the method.

One such spectrophotometric method is based on the recognition that the measurement signal and the reference signal each consists of three signal components—a dark signal component corresponding to the signal generated by the signal detectors when not being struck by any radiation, a direct current component, and an alternating current component corresponding to the signals generated by the detectors when being struck by the modulated radiation. The inventive method is also based on the ratio between the alternating current component and the direct current component being independent of the concentration and known through the degree of modulation of the radiation. In addition to the steps set forth at the outset, the inventive method further comprises the steps of filtering out the measurement signal's alternating current component in the signal analyzer, determining the direct current component from the alternating current component and the known ratio, normalizing the direct current component with the reference signal, and determining the concentration of the specific substance from the normalized direct current component.

Utilization of the direct voltage component makes the use of high frequencies possible, compared to the frequencies stated for the known spectrophotometer, for determining the concentration of the specific substance. The direct voltage component is larger at high frequencies than the alternating current component, since modulation has decreased. For a specific radiation source, a direct current component at 200 Hz could be, e.g., 10 times larger than the alternating current component. This results in a better signal-to-noise ratio for the direct current component than for the alternating current component. The alternating current component is determined first so the direct current component can be filtered out. The direct current component can subsequently be determined from the known ratio obtained from the known degree of modulation.

One advantageous way of establishing the direct current component is achieved in an embodiment of the invention wherein a value for the direct current component is calculated from the alternating current component and the known ratio, a value for the dark signal component is determined by subtracting the value calculated for the direct current component from the measurement signal less the alternating current component, the measurement signal's direct current component is filtered out by subtracting the value calculated for the dark signal component and eliminating the alternating current component from the measurement signal.

The direct current signal can be filtered out of the measurement signal by determination of the dark signal component. Since the dark signal component depends on, inter alia, the temperature of detectors, continuous determination of the dark signal component would be an advantage in order to eliminate it from the measurement signal when the direct current component is to be filtered out. The time for determining the dark signal component should be brief in relation to variations in detector temperatures. The dark signal component is established by first determining the magnitude of the alternating current component. A value for the direct current component can be calculated, since the ratio between the alternating current component and the direct current component at any given point in time is known for a given radiation source and modulation frequency. With two known signal components, the third component, i.e., the dark signal component, can be calculated. The value calculated for the dark signal component is then used for determining the direct current component from the measurement signal. The value calculated for the direct current component is not utilized for determining the concentration, since the relatively high level of noise in the alternating current component is amplified as much as the signal itself. In addition, signal spikes in the alternating current component can develop when there are rapid fluctuations in concentration, and these signal spikes should be avoided. Compared to the state of the art, the invention is more tolerant of rapid fluctuations in concentration without error, since its response time is shorter.

An improvement of the method is achieved in accordance with the invention in an embodiment wherein the alternating current component of the reference signal is filtered out, and normalization of the direct current component of the measurement signal is performed using the alternating current component.

The reference signal is not affected by changes in concentration and is therefore used to normalize the measurement signal's direct current component. It can therefore be filtered to a greater extent to obtain an alternating current component with a better signal-to-noise ratio than the measurement signal's direct current component. An AC filter is easier to achieve in analog circuits.

Alternatively, the method can be performed so the reference signal's direct current component is determined by filtering out the direct current component. A value for the direct current component is then determined from the alternating current component and the known ratio. A value for the dark signal component is determined by subtracting the value determined for the direct current component from the reference signal less the alternating current component. The direct current component of the reference signal is filtered out by subtracting the value determined for the dark signal component and eliminating the alternating current component from the reference signal, and the direct current component of the measurement signal is normalized with the direct current component of the reference signal.

The direct current component has the best signal-to-noise ratio, also in the reference signal. In some instances, a good signal-to-noise ratio is also required for the reference signal while response time is simultaneously brief. Moreover, this ratio gives access to the reference signal's dark signal component. Comparing the measurement signal's dark signal component with the reference signal's dark signal component provides additional monitoring of the ray path and detector function. If e.g., the temperature of only one detector changed, the ratio between the dark signal components would change, designating a fault. This would also be the case if soiling or condensation blocked a part of the path of the ray between the source of radiation and one of the detectors. The dark signal components could also be used for regulating the temperature of the detectors.

A further improvement of the method is achieved in an embodiment wherein the current degree of modulation is calculated by a control device, and the calculated current degree of modulation is used by the signal analyzer for determining the value of the direct current component from the alternating current component and the known ratio between the alternating current component and the direct current component.

In this manner, the signal analyzer can automatically correct the concentration calculation when the degree of modulation changes. Changes could, e.g., occur when the source of radiation is an incandescent lamp whose filament has a thermal time constant which changes as the filament ages as filament material boils off the filament. With a constant modulation frequency, the current degree of modulation of an incandescent lamp mainly depends on the thermal time constant.

One advantageous way of calculating the current degree of modulation is by analyzing the conformation of the curve for the alternating current component. The reference signal is independent of the concentration of the specific substance and is therefore more suitable to use than the measurement signal.

The alternating current consists of rising and falling exponential curves dependent on thermal time constant of the source of radiation. The time constant can be determined from these exponential curves, and the exact ratio between the alternating current component and the direct current component can be calculated.

An alternative way of calculating the current degree of modulation is achieved in accordance with the invention in an embodiment wherein a modulated current from a current supply is applied to the source of radiation, the current from the current supply is interrupted for at least one modulation period, the alternating current component of the reference signal is recorded for subsequent modulation periods and the control device analyzes changes in the alternating current component, calculating the current degree of modulation from this change.

When current to the source of radiation is interrupted for at least one modulation period, the source cools slightly, and a certain amount of time elapses before the temperature of the source of radiation returns to normal after current is re-applied. Recording the way in which the alternating current component reacts during the time temperature deviates from the normal, and thus how rapidly the source of radiation reverts to its normal temperature, makes it possible to calculate the thermal time constant and, accordingly, the current degree of modulation.

A further alternative procedure is achieved in an embodiment wherein radiation from the source of radiation is detected with an additional reference detector, whose dark signal component is negligible and which generates a signal consisting of a direct current component and an alternating current component. The two voltage components are separated and the current degree of modulation is established by determining the ratio between them.

There are several types of known photodetectors. When the concentration of a specific substance is determined, a good signal-to-noise ratio is essential, and the detector must be designed for a spectral range in which the specific substance has an absorption wavelength. Photoresistors, for example, generate signals containing three components when the radiation is modulated. The dark signal component predominates in that type of photodetector. Another type of photodetector is the photodiode which, in contrast to the photoresistor, produces a small dark signal component, especially when it is connected as a current generator. In modulated radiation, mainly two signal components are obtained. The radiation can be detected at wavelengths other than those at which measurement of concentration is performed in order to determine the current degree of modulation. For example, a photodiode may be useless for measuring the concentration of a specific substance, depending on its absorption wavelength, but fully adequate for generating a signal from which the degree of modulation can be determined at another wavelength. According to Planck's radiation law, the degree of modulation at the absorption wavelength for a specific substance can be calculated and used.

Yet another alternative way of obtaining the current degree of modulation is achieved when a filament is employed as a source of radiation. Variations in the resistance of the filament are then measured during the period of modulation and the current degree of modulation is determined from measured variations in resistance.

The filament's temperature determines the spectral distribution and intensity of the radiation. When a modulated current is applied to the filament, the filament's temperature will vary between two levels, giving rise to pulsed radiation. The temperature gradient between the two levels determines the degree of intensity modulation. Since the filament's resistivity, and accordingly its resistance, are temperature-dependent, resistance may be utilized for determining the degree of modulation. Variations in resistance can be measured by measuring the current through and voltage across the filament.

In addition to a spectrophotometric method, a spectrophotometer apparatus is disclosed, operating according to the above-described method. A first embodiment of the spectrophotometer of the invention for measuring the concentration of a substance includes a radiation source which emits radiation having an intensity which is modulated with a selected degree of modulation. The radiation passes through the substance whose concentration is to be measured, and the radiation is then incident on a first detector and on a second detector. The first detector detects radiation at a wavelength at which the specific substance absorbs, and generates a corresponding measurement signal $U_{meas}$. The second detector detects radiation at a wavelength different from the absorption wavelength for the substance in question, and generates a reference signal $U_{ref}$. The respective signals of the first and second detectors are supplied to a signal analyzer. The measurement signal $U_{meas}$ and the reference signal $U_{ref}$ each consist of three signal components. The first of these components is a dark signal component $U_0$, which corresponds to the signal generated by each of the first and second detectors when not being struck by any radiation. The second signal is a direct current component $U_{DC}$. The third component is an alternating current component $U_{AC}$, corresponding to the signals generated by the first and second detectors when struck by the modulated radiation. The ratio between the alternating current component $U_{AC}$ and the direct current component $U_{DC}$ is independent of the concentration, and is known by the degree of modulation to which the radiation was subjected. The signal analyzer includes a first signal conditioning device for filtering out the alternating current component $U_{measAC}$ of the measurement signal, and the direct current component of the measurement signal $U_{measDC}$ is determined from the alternating current component $U_{measAC}$ and the known ratio. The signal analyzer also includes a second signal conditioning device for determining a normalization factor from the reference signal $U_{ref}$, and a control device for normalizing the direct current component $U_{measDC}$ with the normalization factor, and for calculating the concentration of the specific substance from the normalized direct current component $U_{measDC}$.

The control device may include means for calculating the current degree of modulation of the radiation from the radiation source, and the first signal conditioning device can then determine the direct current component $U_{measDC}$ from the alternating current component $U_{measAC}$ and the calculated degree of modulation.

In a further embodiment of the spectrophotometer of the invention the first signal conditioning device includes a first measurement signal channel with, inter alia, a signal amplifier which amplifies the measurement signal by a selected first gain, a first differential amplifier in which the dark signal component, amplified with the first gain, is subtracted from the amplified measurement signal, and a first integrator in which the alternating current component is eliminated. The spectrophotometer in this embodiment also includes a second measurement signal channel with, inter alia, a first signal filter for filtering out the alternating current component, an amplifier which amplifies the alternating current component with a selected second gain, a second differential amplifier to which the first integrator and amplifier are connected, and a second integrator which integrates the output signal from the second differential amplifier. The first gain and the second gain are selected such that the direct current component amplified with the first gain is identical in magnitude to the alternating current component amplified with the second gain. The output signal from the first integrator is equal to the dark signal component amplified with the first gain and connected to the first differential amplifier.

With an analog circuit coupling according to the described embodiment, a servo loop is obtained which automatically strives to continuously determine the dark signal component and subtract same from the measurement signal, so the direct current component can be filtered out. At the same time, the servo loop ensures that even if the defined gains are incorrect because the ratio between the alternating current component and the direct current component changes, as can occur because of, e.g., aging of the source of radiation or some error in determination of the degree of modulation, the servo loop still compensates for this error so the direct current component is adapted to the alternating current component. This is because a slight difference between the direct current component and the alternating current component, each with its respective selected gain, causes the integrator to calculate, e.g., a value for the dark signal component which is larger than the true dark signal component, leading to subtraction of a somewhat larger signal from the measurement signal and causing the direct current component to decline and to be adapted to the alternating current component. The integrator has a time constant which is large in relation to the modulation frequency but small in relation to changes in the temperature of the detectors. Thus, the integrator calculates the dark signal component with a slight delay but with a sufficient accuracy.

A further improvement of the spectrophotometer of the invention is achieved in another embodiment wherein the signal analyzer further includes a first averager for sequentially averaging the measurement signal's direct current component over a short period of time, preferably one modulation period, and a second averager for sequentially averaging the amplitude for the reference signal's alternating current component for the period of time. The control device then sequentially calculates the concentration of the specific substance, from the average value for the direct current component and the average value for the amplitude of the reference signal.

Averaging in every signal period results in normalization of the direct current component with the alternating current component, and calculation of the concentration is facilitated.

For the spectrophotometer according to the present invention, it is preferable that the modulated radiation from the source of radiation has a frequency between 50 and 1000 Hz.

The lower frequency limit depends on the magnitude of the acceptable response time and the frequency at which modulation is such that the alternating current component becomes larger than the direct current component and, therefore, more suitable for use. The upper frequency limit can be considerably higher than 1000 Hz and depends on the ability of the source of radiation to emit the radiation pulsed with a degree of modulation sufficient to enable removal of the alternating current component and at a frequency the detectors can accommodate.

A further improvement of the spectrophotometer of the invention is achieved in an embodiment wherein the signal analyzer includes a measurement signal channel with a protective filter which senses the measurement signal's alternating current component and eliminates segments of the alternating current component containing deviations from the normal curve conformation.

Eliminating interference in the alternating current component prevents this noise from affecting determinations of the different components, thereby preventing errors in calculation of the direct current component and the concentration of the specific substance. Such signal errors can occur, e.g., when the concentration changes very rapidly, i.e., when the direct current component is not eliminated when the alternating current component is filtered out.

Preferably, the protective filter is formed by an integrator, a comparator and a switch. The switch is arranged to prevent, when open, deviations in the alternating current component from affecting determination of the direct current component. The integrator integrates the alternating current component for each modulation period and the comparator compares the absolute magnitude of the integrated value for each period with a defined limit value. The switch opens when the limit value is exceeded, for at least the time during which the limit value is exceeded.

Integration of the alternating current component for one modulation period normally produces a zero signal, except for noise, since the alternating current component has a positive part which is as large as the negative part. When signal interference, e.g., signal spikes, occur, the integration result deviates from zero. If the deviation is sufficiently large, the switch opens to prevent signal interference from passing on to the rest of the signal analyzer. The permissible deviation can be set so close to zero that all deviations exceeding normal noise cause the switch to open. This can be appropriate when a servo loop is used for filtering out the direct current component. The servo's integrator of the servo loop, which determines the dark signal component, is then not affected by signal interference.

DESCRIPTION OF THE DRAWINGS

FIG. 4 shows an alternative embodiment of a part of the spectrophotometer of the invention for determining a degree of modulation.

DESCRIPTION OF THE PREFERRED EMBODIMENTS

Figure 1:
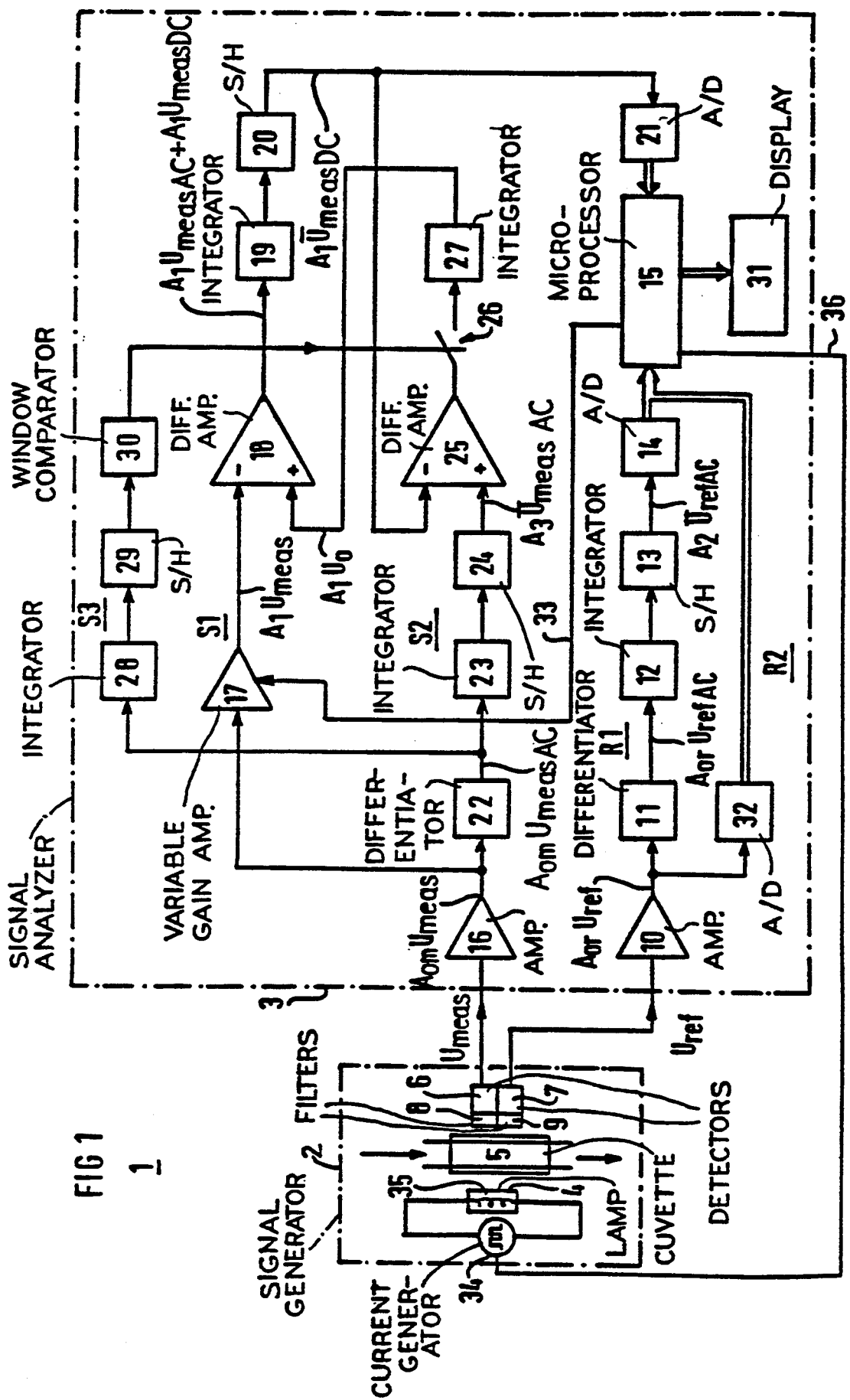
FIG. 1 is a schematic block diagram of one embodiment of a spectrophotometer constructed and operating in accordance with the principles of the present invention.

The spectrophotometer 1 shown in FIG. 1 has a signal generator 2 and a signal analyzer 3. The spectrophotometer 1 will henceforth be described as a $CO_2$ analyzer in a respirator/ventilator (not shown) to facilitate explanation of its function and design. The spectrophotometer 1, however, is not restricted to this use and can, with the same general design, be used for all types of analyses of a specific substance in a mixture of a plurality of substances, provided the specific substance absorbs radiation at least one wavelength at which other substances in the mixture do not absorb any radiation (unless measurement is undertaken of the other substances at wavelengths at which only they absorb radiation, the calculation of concentration being adjusted accordingly).

The signal generator 2 has an incandescent lamp 4 with a filament 35 to which a pulsating current from a current generator 34 is applied. The pulsation frequency is relatively high, preferably above 50 Hz. The frequency is 200 Hz in the following example. The high frequency means that the intensity of radiation from the incandescent lamp 4 exhibits a waveform which is primarily triangular. Radiation passes through a specimen cuvette 5 containing some of the gas to be analyzed. A first radiation-sensitive detector 6 and a second radiation-sensitive detector 7 are arranged in the path of the radiation following the specimen cuvette 5. In this instance, when $CO_2$ is to be measured, the detectors 6 and 7 consist of PbSe photoresistors. A defined current is passed through the respective photoresistors, and the ensuing voltage constitutes a signal which is evaluated by the signal analyzer 3. When no radiation strikes the detectors 6 and 7, a dark signal is obtained which only depends on the temperature of the detectors 6 and 7.

Figure 2:
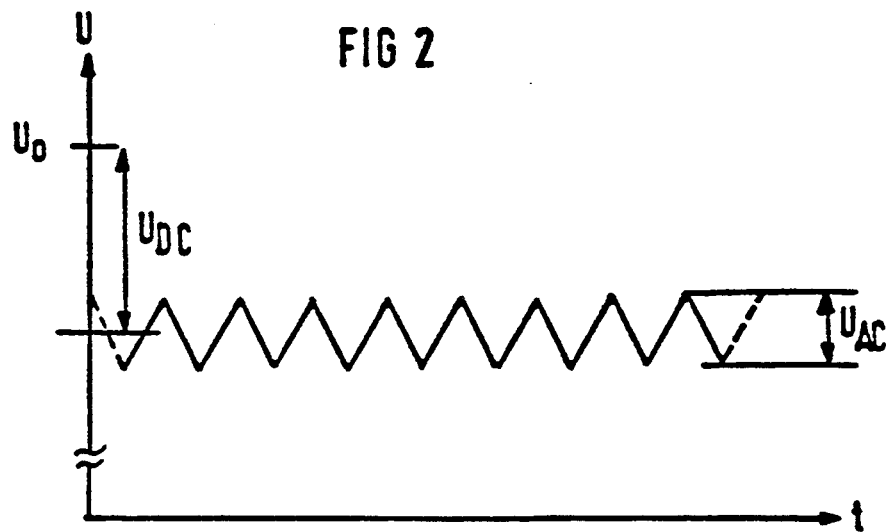
FIG. 2 schematically shows three signal components in a measurement signal generated by the spectrophotometer of the invention.

For the dark signals from the detectors 6 and 7 to be as equal as possible, the detectors 6 and 7 are placed near one another and in thermal contact but without radiation in the radiation path for one detector being able to strike the other. A temperature regulation system (not shown) regulates the temperature of the detectors 6 and 7 and keeps it constant, preferably at 40° C., to prevent condensation from forming on the specimen cuvette 5 and thereby to reduce dark signal drift. When radiation strikes the detectors 6 and 7, their resistance decreases, and the voltage across the detectors 6 and 7 changes. Since the radiation has a triangular waveform, as noted above, the voltage signal U, as shown in FIG. 2, will consist of a direct current component $U_{DC}$ and an alternating current component $U_{AC}$ superimposed on the dark signal $U_0$. The relative magnitude of these three signal components depends on, e.g., the operating temperature of the detectors 6 and 7, the intensity of the incandescent lamp 4 and the time constant of the filament 35. In this instance, the alternating current component $U_{AC}$ is about 1/10 the size of the direct current component $U_{DC}$ which, in turn, is about 1/100 the size of the dark signal component $U_O$.

A first filter 8 is placed in front of the first detector 6. This first filter 8 is transparent to radiation wavelengths at which $CO_2$ absorbs radiation, in this instance 4.26 μm. In the corresponding manner, a second filter 9 is placed in front of the second detector 7. The second filter 9 is transparent to radiation wavelengths at which $CO_2$ does 16 not absorb, e.g., 3.40 μm. The second filter 9 can also be selected so it is transparent to a wider range of wavelengths. As a result, the voltage signal U obtained from the first detector 6 depends on the amount of $CO_2$ in the gas in the specimen cuvette 5 and is further used as the measurement signal $U_{meas}$, whereas the voltage signal U from the second detector 7 is independent of the amount of $CO_2$, thereby constituting a reference signal $U_{ref}$. All other external factors, such as temperature variations, soiling or condensation in the specimen cuvette 5 and variations in the intensity of radiation from the incandescent lamp 4, will affect the measurement signal $U_{meas}$ and the reference signal $U_{ref}$ to an equal degree. However, this assumes that the detectors 6 and 7 are affected by external factors to the same extent. By normalization of the measurement signal $U_{meas}$ with the aid of the reference signal $U_{ref}$, the concentration of $CO_2$ in the gas can accordingly be calculated. This is performed in the signal analyzer 3 which contains two reference signal channels R1 and R2 and three measurement signal channels S1, S2 and S3.

In the reference signal channel R1, the reference signal is first amplified in a first preamplifier 10 with a gain $A_{0r}$ and is then differentiated in a first differentiator circuit 11. Differentiation eliminates the dark signal component $U_0$ and the direct current component $U_{refDC}$ from the amplified reference signal $A_{0r}U_{ref}$. The remaining amplified alternating current component $A_{0r}U_{refAC}$ is integrated for one triangular wave period, 5 ms, in a first differential integrator 12. The first differential integrator 12 integrates the signal with a positive sign when the signal is positive and with a negative sign when the signal is negative. This means that the output signal from the first differential integrator 12 becomes the average value for the amplitude of the amplified alternating current component $A_2\overline{U}_{refAC}$ in one period. At the end of the period, the output signal from the first differential integrator 12 is sampled in a first sample and hold circuit 13 which emits the amplified signal as an output signal in the next period. When the first sample and hold circuit 13 has sampled the signal, the first differential integrator 12 is zeroed in order to integrate the alternating current component $U_{refAC}$ in the next triangular wave period. The signal at the output terminal of the sample and hold (S/H) circuit 13 is thus the average value of the amplitude of the alternating current component $A_2\overline{U}_{refAC}$, with a selected first amplification. This signal is digitized in a first A/D converter 14 and fed into a microprocessor 15 for normalization of the measurement signal $U_{meas}$ from the detector 6.

Conditioning of the measurement signal $U_{meas}$ will be described below. As noted above, the alternating current component $U_{measAC}$ is 1/10 of the direct current component $U_{measDC}$. This ratio depends on the filament 35 of the incandescent lamp 4 and changes as the filament 35 ages, as described below. Since both the direct current component $U_{measDC}$ and the alternating current component $U_{measAC}$ depend on the $CO_2$ concentration, eliminating the direct current component $U_{measDC}$ is difficult when there are rapid fluctuations in $CO_2$ concentration. Rapid fluctuations in the $CO_2$ content occur at every transition from inspiration to expiration and vice-versa. Thus, conditioning the measurement signal in the same way as the reference signal $U_{ref}$ would cause the ten times larger direct current component $U_{measDC}$ to interfere with determination of the magnitude of the alternating current component $U_{measAC}$, and thus with calculation of the $CO_2$ concentration, when there are rapid fluctuations in concentration. In addition, the alternating current component $U_{measAC}$ has a poorer signal-to-noise ratio than the direct current component $U_{measDC}$. The signal-to-noise ratio can be improved for the alternating current component $U_{measAC}$ by e.g., increasing the current through the incandescent lamp 4, but this would simultaneously accelerate the aging of the incandescent lamp 4. Alternatively, the pulsation frequency of the current from the current generator 34 to the incandescent lamp 4 could be reduced so that modulation of intensity increases, but this would reduce the measuring unit's response time. PbSe detectors are known to have a frequency "knee". For frequencies under the "knee" frequency, noise is inversely proportional to the frequency, i.e., by a factor of 1/f, where f is the frequency. The frequency "knee" for PbSe detectors is generally under 50 Hz.

To avoid these problems, the direct current component $U_{measDC}$ is instead filtered out of the measurement signal $U_{meas}$ in the manner described below.

The measurement signal $U_{meas}$ is first amplified in a second preamplifier 16 with a gain $A_{0m}$. The amplified measurement signal $A_{0m}U_{meas}$ is then passed through two measurement signal channels 81 and 82. In the first measurement signal channel S1, the measurement signal $A_{0m}U_{meas}$ is further amplified in a variable gain amplifier 17, and the amplified measurement signal $A_1U_{meas}$ is sent to the negative input terminal of a first differential amplifier 18. The dark signal component $U_0$, with the same gain $A_1$ as the measurement signal $U_{meas}$, is coupled to the positive input terminal, so that only the direct current and the alternating current components $A_1U_{measDC}$, $A_1U_{measAC}$ remain after the first differential amplifier 18. A more detailed description of how the dark signal component $U_0$ is obtained is provided below.

After the first differential amplifier 18, the remaining measurement signal $A_1(U_{measAC}+U_{measDC})$ in every triangular wave period is integrated in a first integrator 19 so as to eliminate the alternating current component $U_{measAC}$ and reduce noise. Integration is followed by sampling in a second sample and hold circuit 20 at the end of each period. Thus, the output signal from the second sample and hold circuit 20 consists of the average of the direct current component $A_1\overline{U}_{measDC}$, with a selected gain, for every triangular wave period. This signal is sent to a second A/D converter 21 for digitization and then enters the microprocessor 15. Each new signal value $A_1\overline{U}_{measDC}$ from the second A/D converter 21 is normalized in the microprocessor 15 with the corresponding input signal $A_2\overline{U}_{refAC}$ from the first A/D converter 14, providing a pure concentration-dependent $CO_2$ signal. Dependent on the way this $CO_2$ signal is affected by known concentrations of $CO_2$, a ratio can be established from which the concentration of $CO_2$ can be calculated for each $CO_2$ signal value. The value obtained for the $CO_2$ concentration can then be presented in real time on a display 31, which can be an LCD screen, a bar graph, a printer or the like. The values can also be stored in the memory of the microprocessor 15 or in an external computer unit for, e.g., more detailed study of a specific patient's $CO_2$ concentration over a long period of time.

As noted above, the amplified dark signal component $A_1U_0$ must be subtracted from the amplified measurement signal $A_1U_{meas}$ in the first differential amplifier 18 for the measurement to work properly. One way of doing this is to shield the detector 6 from external sources of radiation, measure the dark signal component $U_0$ at the operating temperature and then apply a voltage to the positive input terminal in the first differential amplifier 18 corresponding to the dark signal component $U_0$ with the gain $A_1$ given the measurement signal $U_{meas}$ in the preamplifier 16 and the variable gain amplifier 17. The measurement would then be dependent on the temperature. To avoid this, the dark signal component $U_0$ is continuously calculated in the spectrophotometer 1.

Figure 3:
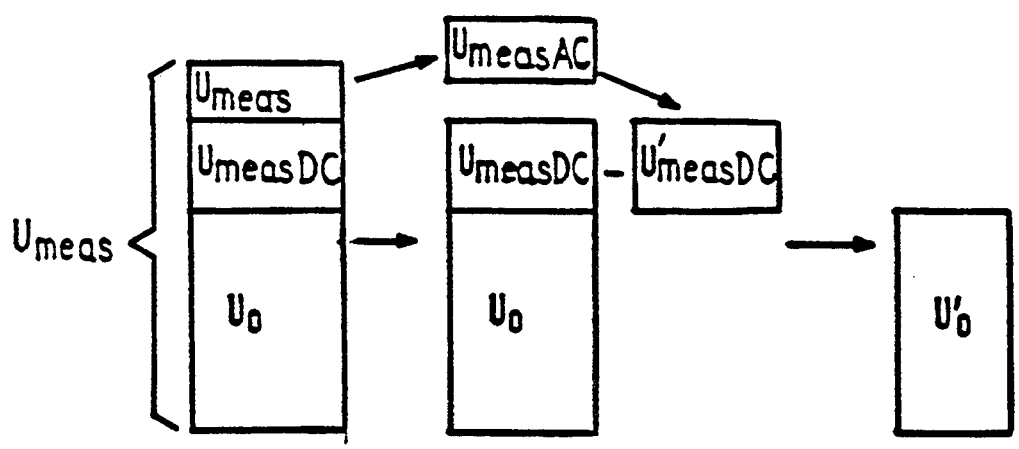
FIG. 3 schematically shows how the measurement signal is conditioned.

In FIG. 3 schematically shows the way in which the dark signal component $U_0$ is determined from the measurement signal $U_{meas}$. The measurement signal $U_{meas}$ consists of three signal components, i.e., the alternating current component $U_{measAC}$, the direct current component $U_{measDC}$ and the dark signal component $U_0$. The alternating current component $U_{measAC}$ is filtered out of the other components, and a virtual direct current component $U'_{measDC}$ can be calculated from the known ratio between the alternating current component $U_{measAC}$ and the direct current component $U_{measDC}$ which is governed by the degree of modulation of radiation from the incandescent lamp 4. The virtual direct current component $U'_{measDC}$ is subtracted from the remaining two signal components $U_{measDC}+U_0$ and provides a virtual dark signal component $U'_0$. If the ratio between the alternating current component $U_{measAC}$ and the direct current component $U_{measDC}$ is accurately determined, the virtual dark signal component $U'_0$ will have the same value as the dark signal component $U_0$. The reason why the virtual direct current component $U'_{measDC}$ is not used as the signal for determining the $CO_2$ concentration is because the alternating current component $U_{measAC}$ has a poorer signal-to-noise ratio, and the virtual direct voltage component $U'_{measDC}$ would accordingly have a poorer signal-to-noise ratio than the true direct current component $U_{measDC}$.

The spectrophotometer 1 is devised as follows in order to determine the dark signal component $U_0$.

It was noted above that the amplified measurement signal $A_{0m}U_{meas}$ is passed through two measurement signal channels S1 and S2 after the preamplifier 16. In principle, the second measurement signal channel S2 is identical to the reference signal channel R1. The measurement signal $A_{0m}U_{meas}$ is differentiated in a second differentiator 22 in order to filter out the alternating current component $A_{0m}U_{measAC}$, which is then integrated in every triangular wave period in a second differential integrator 23. The integrator 23 integrates the signal with a positive sign when the signal is positive and with a negative sign when the signal is negative. This means that the output signal from the second differential integrator 23 is the average value for the amplitude of the amplified alternating current component $A_3\overline{U}_{measAC}$ in one period. At the end of each period, the signal from the second differential integrator 23 is sampled in a third sample and hold circuit 24, whereupon the second differential integrator 23 is zeroed and begins integrating the next triangular wave period. The output signal from the third sample and hold circuit 24 thereby consists of the average amplitude for each period of the alternating current component $A_3\overline{U}_{measAC}$ with a defined gain, and this constitutes the input signal to the positive input terminal of a second differential amplifier 25. The signal from the second sample and hold circuit 20 is connected to the negative input terminal of the second differential amplifier 25, i.e., the average value for each period of the direct current component $A_1\overline{U}_{measDC}$ with a selected gain. The output signal from the second differential amplifier 25 is an error signal which designates the difference between the virtual direct current component $U'_{measDC}$ and the true direct current component $U_{measDC}$.

A switch 26, which is normally closed and whose function is described below, follows the second differential amplifier 25 and is in turn followed by a regulating integrator 27, which has a time constant that is much longer than the period duration, e.g., 1 sec., and which integrates the error signal. As long as the error signal is zero, the output signal of the integrator 27 remains constant. The output signal from the regulating integrator 27 is connected to the positive input terminal of the first differential amplifier 18. When the measurement signal $U_{meas}$ is initially generated in the system, the output signal from the regulating integrator 27 is zero, and the entire amplified measurement signal $A_1U_{meas}$ passes the first differential amplifier 18. The alternating current component $U_{measAC}$ is eliminated in the first integrator 19, and the output signal from the subsequent second sample and hold circuit 20 consists of the amplified average of the dark signal component $A_1\overline{U}_0$ and the direct current component $A_1U_{measDC}$ for each period. The first integrator 19 also reduces noise in the input signal. This signal is returned to the negative input terminal of the second differential amplifier 25. As noted above, the output signal from the third sample and hold circuit 24, consisting of the amplified average of the alternating current component $A_3\overline{U}_{measAC}$ for each period, is connected to the positive input terminal. The difference between the two signals, i.e., the error signal, is fed into the regulating integrator 27 which thereby emits an output signal which rapidly increases. This increase causes the signal after the first differential amplifier 18 to decrease, causing, in turn, the error signal after the second differential amplifier 25 to decline.

Selection of the gains $A_1$ and $A_3$ so that the average value for the amplified direct current component $A_1\overline{U}_{measDC}$ and the average value of the amplitude of the amplified alternating current component $A_3\overline{U}_{measAC}$ are equal makes the signal after the regulating integrator 27 the same as the dark signal component $U_0$ amplified with the gain $A_1$ given the measurement signal $U_{meas}$ in the preamplifier 16 and the variable amplifier 17. The time constant for the regulating integrator 27 is long compared to the modulation period, e.g., 1 second. This means that the dark signal component $U_0$ determined in this manner consists of dark signal components from previous times in real time. Since the detectors 6 and 7 are temperature-regulated, the value of the dark signal component $U_0$ is unable to change rapidly, making the value as determined above more accurate. The gains $A_1$ and $A_3$ are selected on the basis of the known ratio, i.e., the degree of modulation. The signal after the first differential amplifier 18 only consists of the direct current and alternating current components $A_1U_{measDC}$ and $A_1U_{measAC}$, and the error signal after the second differential amplifier 25 will be equal to zero, so the regulating integrator 27 retains the output signal $A_1U_0$. Owing to small losses in circuit components, the different signals will oscillate around the desired values, but as soon as the error signal after the second differential amplifier 25 deviates from zero, the regulating integrator 27 corrects its output signal so the error signal again becomes zero. Thus, feedback provides a servo loop which continuously strives to retain the signal component $U_0$ with its defined gain $A_1$ as an output signal.

The above described signal conditioning for determining the dark signal component $U_0$ and filtering out the direct current component $U_{measDC}$ could be performed in a circuit without feedback. However, servo feedback ensures that the virtual direct current component $U_{measDC}$, whose signal-to-noise ratio is low, is fed back via the regulating integrator 27 and the first integrator 19, thereby reducing the noise which would otherwise be superimposed on the direct current component $U_{measDC}$.

If the variable amplifier 17 is incorrectly set, which is possible when the ratio between the direct current and alternating current components $U_{measDC}$ and $U_{measAC}$ in radiation from the incandescent lamp 4 changes as the incandescent lamp's 4 filament 35 ages, the error signal after the second differential amplifier 25 will deviate from zero when concentration changes. Integration by the regulating integrator 27 then produces an erroneous value for the dark signal component $U_0$, but since integration continues until the error signal is again zero, the average value for the direct current component $A_1\overline{U}_{meas}$ will be adapted to the average value of the alternating current component $A_3\overline{U}_{measAC}$ and produce a correct measurement value for the concentration of $CO_2$. When the concentration of $CO_2$ changes at the transition from inspiration to expiration and vice-versa virtually in stages, stage response will be erroneous, however.

Even if the variable amplifier 17 is correctly set, interference may develop in the measurement signal $U_{meas}$. As noted above, the direct current component $U_{measDC}$, for example, is not easily separated from the alternating current component $U_{measAC}$ when concentration fluctuates rapidly. The average value of the alternating current component $A_3\overline{U}_{measAC}$ will then be erroneous. To prevent this error from passing the second differential amplifier 25 and affecting integration in the regulating integrator 27, the switch 26 has been placed between these two circuits. The signal after the second differentiator 22 is diverted to a third measurement signal channel S3 to control the switch 26. This signal consists of the amplified alternating current component $A_0U_{measAC}$. The signal is integrated in every triangular wave period by a second integrator 28, and at the end of each period, output signals from the second integrator 28 are sampled in a fourth sample and hold circuit 29. As long as there is no interference in the measurement signal, the output signal from the fourth sample and hold circuit 29 will, in principle, be equal to zero. Essentially, only noise occurs as an output signal. When interference, e.g., in the form of a signal spike in the alternating current component $U_{measAC}$, occurs, the output signal from the second integrator 28 at the end of the period differs from zero, and this signal becomes the output signal from the fourth sample and hold circuit 29 in the next period. This signal is sent to a window comparator 30 which opens the switch 26 when the signal from the fourth sample and hold circuit 29 deviates from a limit range around zero. The error signal from the second differential amplifier 25 will then fail to reach the regulating integrator 27, and the interference will not affect the output signal from the integrator 27. The switch 26 is kept open as long as the interference lasts. The window comparator 30 suitably emits a pulse which keeps the switch 26 open for a defined minimum period of time. However, the first measurement channel's S1 output signal, from the second sample and hold circuit 20, i.e., the average value of the direct current component $A_1\overline{U}_{measDC}$, will display the rapid signal fluctuations and supply a correct measurement value.

To prevent the development of errors in the variable amplifier 17 as the incandescent lamp 4 ages, the signal analyzer 3 is provided with a self-calibration function for setting the gain of the variable amplifier 17. After the first preamplifier 10, the reference signal channel R1 branches off into the second reference signal channel R2. The amplified reference signal $A_0U_{ref}$ is sent in the second reference signal channel R2 to a third A/D converter 32, and the digitized reference signal $A_0U_{ref}$ is sent to the microprocessor 15. In the microprocessor 15, the alternating current component $U_{refAC}$, which consists of alternately rising and falling exponential curves, is analyzed. These exponential curves depend on the time constant for the incandescent lamp's 4 filament 35. The time constant can be calculated by averaging a large number of curves. This also yields the degree of modulation which, at a constant pulsation frequency, depends only on the time constant. When a change in the time constant then occurs, e.g., because the filament material boils off the filament 35, the microprocessor 15 can calculate, on the basis of changes in the time constant, how much the gain of the variable amplifier 17 is to be changed, and can institute the changes via a control line 33.

In the above, one embodiment was described in which the invention was devised as an analog circuit. It is also fully possible to supply the measurement signal $U_{meas}$ and reference signal $U_{ref}$, immediately after the detectors 6 and 7, to a respective A/D converters wherein they are digitized for subsequent analysis and processing in a microprocessor or some other computer unit in a manner equivalent to the one described above.

Calculation of the time constant for determination of the ratio between the alternating current component $U_{AC}$ and the direct current component $U_{DC}$ can also be performed in other ways. In FIG. 1, another method is suggested by a control line 36 from the microprocessor 15 to the current generator 34, through which the microprocessor 15 can control the current generator 30. The filament 35 cools slightly when the flow of current from the current generator 30 is interrupted for at least one pulsation period. When pulses of current are reapplied to the filament 35, the temperature of the filament 35 rises towards the temperature it had before the incandescent lamp 4 was switched off. The time constant for the filament 35 can be determined by measuring the change in the reference signal's alternating current component $U_{refAC}$ during the return to the operating temperature.

The setting of the variable amplifier 17 can also be controlled by preventing, for a very brief period of time, radiation from the source of radiation 4 from reaching the first detector 6. The signal to the microprocessor 15 will then be zero if a correct gain has been set.

FIG. 4 shows a third way of determining the time constant or degree of modulation. FIG. 4 only shows the necessary elements from FIG. 1. In other respects, the spectrophotometer is identical to the one described in FIG. 1. Pulses of current from the current generator 34 are applied to the incandescent lamp 4 with the filament 35. The radiation passes through the specimen cuvette 5 and the filters 8 and 9 and hits the detectors 6 and 7. Signals are sent from the detectors 6 and 7 to the signal analyzer 3. A photodetector 37 is located by the incandescent lamp 4, outside the path of radiation from the incandescent lamp 4 to the detectors 6 and 7. The photodetector 37 has a dark signal component $U_0$ which is negligible, and consists, e.g., of a photodiode 37 connected as a current generator and sensitive to radiation at the intensity maximum for the filament 35. At this wavelength, the intensity of the filament 35 is sufficient for the gain of the photodiode 37 to produce a signal with an adequate signal-to-noise ratio. As a result of the modulated radiation, the photodiode 37 generates a signal consisting of an alternating current component and a direct current component. In a fourth A/D converter 38, the signal is digitized and fed into the microprocessor 15 in which the signal is divided into the respective components, and the ratio between the alternating current component and the direct current component can be determined. On the basis of Planck's radiation law, the microprocessor 15 can calculate the ratio at the wavelengths at which measurement of concentration is made.

Although modifications and changes may be suggested by those skilled in the art, it is the intention of the inventors to embody within the patent warranted hereon all changes and modifications as reasonably and properly come within the scope of their contribution to the art.

We claim as our invention:

1. A spectrophotometric method for determining the concentration of a substance, comprising the steps of:
    directing radiation having a selected degree of intensity modulation through a substance whose concentration is to be determined, said radiation including radiation at a wavelength absorbed by said substance and other radiation;
    detecting said radiation, after passing through said substance, at said wavelength absorbed by said substance with a first detector and generating a measurement signal corresponding thereto;
    detecting said other radiation after passing through said substance with a second detector and generating a reference signal corresponding thereto, each of said measurement signal and said reference signal consisting of a dark signal component corresponding to respective signals generated by said detectors with no radiation incident thereon, a direct current component and an alternating current component corresponding to respective signals generated by said detectors when said modulated radiation is incident thereon, said alternating current component and said direct current component having a ratio which is independent of the concentration of said substance and which is known from said degree of intensity modulation;
    filtering out said alternating current component from said measurement signal;
    determining said direct current component of said measurement signal from the filtered-out alternating current component and said known ratio;
    normalizing said direct current component of said measurement signal with said reference signal; and
    determining the concentration of said substance from the normalized direct current component.

2. A method as claimed in claim 1 wherein the step of determining the direct current component of said measurement signal is further defined by the steps of:
    calculating a value for said direct current component of said measurement signal from said alternating current component of said measurement signal and said known ratio;
    determining a value for said dark signal component of said measurement signal by subtracting said value calculated for the direct current component from said measurement signal less said alternating current component;
    filtering out the direct current component of said measurement signal by subtracting said value determined for said dark signal component; and
    eliminating said alternating current component from said measurement signal.

3. A method as claimed in claim 1 comprising the additional steps of:
    filtering out the alternating current component of said reference signal; and
    normalizing the direct current component of said measurement signal using said alternating current component of said reference signal.

4. A method as claimed in claim 1 comprising the additional steps, for determining the direct current component of said reference signal, of:
    filtering out said alternating current component from said reference signal;
    determining a value for said direct current component of said reference signal from said alternating current component of said reference signal and said known ratio;
    determining a value for said dark signal component of said reference signal by subtracting said value determined for the direct current component of the reference signal from said reference signal less said alternating current component of said reference signal;
    filtering out the direct current component of the reference signal by subtracting said value determined for the dark signal component of said reference signal and eliminating said alternating current component from said reference signal; and normalizing the direct current component of the measurement signal using the direct current component of said reference signal.

5. A method as claimed in claim 1 comprising the additional steps of:
calculating a current degree of intensity modulation of said radiation; and
determining the value of said direct current component of said measurement signal from said alternating current component of said measurement signal, said current degree of modulation, and said known ratio.

6. A method as claimed in claim 5 wherein the step of calculating the current degree of intensity modulation is further defined by analyzing the waveform of said alternating current component.

7. A method as claimed in claim 5 wherein the step of directing radiation having a selected degree of intensity modulation through said substance is further defined by modulating said radiation at said selected degree of intensity modulation with a modulated current from a current supply, and wherein the step of calculating said current degree of modulation is further defined by the steps of:
interrupting said current from said current supply for at least one modulation period;
measuring the alternating current component of said reference signal in subsequent modulation periods following said at least one modulation period;
analyzing changes in said alternating current component of said reference signal in said subsequent modulation periods; and
calculating said current degree of modulation from changes in said alternating current component during said subsequent modulation periods.

8. A method as claimed in claim 5 wherein the step of calculating said current degree of modulation is further defined by the steps of:
detecting said radiation having a selected degree in intensity modulation using a reference detector having a negligible dark signal component;
generating a direct current component and an alternating current component from said reference detector;
separating said direct current component and said alternating current component from said reference detector; and
determining said current degree of modulation by determining the ratio of said direct current component and said alternating current component of said reference detector.

9. A method as claimed in claim 5 wherein the step of directing radiation having a selected degree on intensity modulation through said substance is further defined by generating said radiation from a radiation source having a filament with a filament resistance which changes over time, and wherein the step of calculating said current degree of modulation is further defined by measuring said filament resistance during periods of said modulation, and determining said current degree of modulation from measured variations in said filament resistance.

10. A spectrophotometer for determining the concentration of a substance, comprising:
means for directing radiation having a selected degree of intensity modulation through a substance whose concentration is to be determined, said radiation including radiation at a wavelength absorbed by said substance and other radiation;
first detector means for detecting said radiation, after passing through said substance, at said wavelength absorbed by said substance with a first detector and for generating a measurement signal corresponding thereto;
second detector means for detecting said other radiation after passing through said substance with a second detector and for generating a reference signal corresponding thereto, each of said measurement signal and said reference signal consisting of a dark signal component corresponding to respective signals generated by said first and second detectors with no radiation incident thereon, a direct current component and an alternating current component corresponding to respective signals generated by said first and second detectors when said modulated radiation is incident thereon, said alternating current component and said direct current component having a ratio which is independent of the concentration of said substance and which is known from said degree of intensity modulation;
first signal conditioning means for filtering out said alternating current component from said measurement signal and for determining said direct current component of said measurement signal from the filtered-out alternating current component and said known ratio;
second signal conditioning means for determining a normalization factor from said reference signal; and
control means for normalizing said direct current component of said measurement signal with said normalization factor and for determining the concentration of said substance from the normalized direct current component.

11. A spectrophotometer as claimed in claim 10 wherein said control means includes means for calculating a current degree of modulation of said radiation, and wherein said first signal conditioning means includes means for determining said direct current component of said measurement signal from said alternating current component of said measurement signal and the calculated degree of modulation.

12. A spectrophotometer as claimed in claim 10 wherein said first signal conditioning means comprises:
a first measurement signal channel having signal amplifier means for amplifying said measurement signal by a first, selected gain, first differential amplifier means, connected to an output of said first amplifier means, for subtracting said dark signal component of said measurement signal, amplified by said first, selected gain, from said measurement signal amplified by said first, selected gain, and first integrator means, connected to an output of said first differential amplifier means, for eliminating said alternating current component of said measurement signal from said output of said first differential amplifier means;
a second measurement channel having first signal filter means for filtering out said alternating current component from said measurement signal, second amplifier means for amplifying the filtered-out alternating current component by a second, selected gain, second differential amplifier means connected to an output of said second amplifier means for subtracting the output of said first integrator means from the output of said second amplifier means;

said first selected gain and said second selected gain being selected so that said direct current component of said measurement signal amplified by said first, selected gain is identical in magnitude with said alternating current component of said measurement signal amplified with said second selected gain so that said output signal from said second integrator means is equal to said dark current component amplified by said first, selected gain.

13. A spectrophotometer as claimed in claim 10 further comprising first averaging means for sequentially averaging the direct current component of said measurement signal over approximately one modulation period of said intensity modulation of said radiation; second averaging means for sequentially averaging the amplitude of the alternating current component of said reference signal over said approximately one period; and said control means including means for sequentially calculating the concentration of said substance from the outputs of said first and second averaging means.

14. A spectrophotometer as claimed in claim 10 wherein said means for directing radiation having a selected degree of intensity modulation through said substance includes a source of radiation at a frequency between 50 and 1000 Hz.

15. A spectrophotometer as claimed in claim 10 further comprising a measurement signal channel with a protective filter means for sensing the alternating current component of said measurement signal and for eliminating portions of said alternating current component of said measurement signal containing deviations from a predetermined normal waveform.

16. A spectrophotometer as claimed in claim 15 wherein said protective filter means comprises:

integrator means supplied with said alternating current component of said measurement signal for integrating said alternating current component of said measurement signal over each modulation period of said intensity modulation of said radiation;

comparator means, connected to an output of said integrator means, for comparing an absolute magnitude of the output of said integrator means for each modulation period with a predetermined limit value; and switch means, controlled by said comparator means to open when said limit value is exceeded, for preventing said alternating current component from reaching said means for determining said direct current component of said measurement signal for at least a period of time during which said limit value is exceeded.

* * * * *